(12) United States Patent
Kang et al.

(10) Patent No.: US 8,162,496 B2
(45) Date of Patent: Apr. 24, 2012

(54) APPARATUS FOR PHOTODYNAMIC DIAGNOSIS OF SKIN DISEASES WITH IMPROVED UNIFORMITY OF ILLUMINATION

(75) Inventors: Uk Kang, Gunpo-si (KR); Soo Jin Bae, Ansan-si (KR); Geun Hie Rim, Changwon-si (KR); Guang Hoon Kim, Busan (KR); Geri. V Papayan, Saint Petersburg (RU)

(73) Assignee: Korea Electro Technology Research Institute, Changwon-Shi, Gyeongsangnam-Do (KR)

( * ) Notice: Subject to any disclaimer, the term of this patent is extended or adjusted under 35 U.S.C. 154(b) by 16 days.

(21) Appl. No.: 11/811,677

(22) Filed: Jun. 11, 2007

(65) Prior Publication Data
US 2008/0180950 A1 Jul. 31, 2008

(30) Foreign Application Priority Data
Jan. 26, 2007 (KR) .......................... 10-2007-0008234

(51) Int. Cl.
G03B 15/02 (2006.01)
(52) U.S. Cl. ...................... 362/11; 362/249.02; 607/90
(58) Field of Classification Search .................. 362/157, 362/184, 200, 202, 227, 230, 231, 240, 555, 362/574, 575, 583, 800, 802, 11, 249.01, 362/249.02, 249.03, 804; 607/90, 92, 93, 607/98, 99, 100, 980, 88, 94, 103; 600/101, 600/109–112, 160–182; 313/498, 500, 501, 313/504, 512
See application file for complete search history.

(56) References Cited

U.S. PATENT DOCUMENTS

| 6,551,240 | B2 * | 4/2003 | Henzler .......................... 600/179 |
| 6,921,920 | B2 * | 7/2005 | Kazakevich ..................... 257/81 |
| 7,279,688 | B2 * | 10/2007 | Campman .................. 250/461.1 |
| 2007/0138966 | A1 * | 6/2007 | Marka et al. ..................... 315/76 |
| 2009/0146080 | A1 * | 6/2009 | Liebsch ..................... 250/484.4 |

FOREIGN PATENT DOCUMENTS

JP 2006198424 A * 8/2006
JP 2006284398 A * 10/2006

* cited by examiner

*Primary Examiner* — Hargobind S Sawhney
(74) *Attorney, Agent, or Firm* — Edwards Wildman Palmer LLP; Peter F. Corless

(57) ABSTRACT

The present invention provides an apparatus for white light observation and fluorescence diagnosis of skin diseases. More particularly, the present invention provides an apparatus for photodynamic diagnosis in which a plurality of excitation light emitting diodes (LEDs) is provided in an image pick-up head, the excitation LEDs being arranged to illuminate the entire examination region in the form of a mosaic by setting respective illumination light axes of the excitation LEDs to illuminate preassigned individual areas of the examination region, thus uniformly illuminating the examination region in a wide field of view with excitation light. In the apparatus for photodynamic diagnosis, the respective excitation LEDs are provided at the same or different angles based on the light axis of the object lens, and thereby it is possible that the beams of the light sources composed of the LEDs illuminate the field of view of the examination region uniformly, thus improving the uniformity of illumination. Moreover, the present invention provides an apparatus for photodynamic diagnosis in which warm white LEDs and cold white LEDs as white light sources are appropriately arranged so as to deliver natural colors and thereby to reproduce natural color images.

12 Claims, 9 Drawing Sheets

< A >   < B >

APPARATUS FOR PHOTODYNAMIC DIAGNOSIS OF SKIN DISEASES WITH IMPROVED UNIFORMITY OF ILLUMINATION

CROSS-REFERENCE TO RELATED APPLICATION

This application claims under 35 U.S.C. §119(a) on Korean Patent Application No. 10-2007-008234 filed on Jan. 26, 2007, the entire contents of which are incorporated herein by reference.

BACKGROUND OF THE INVENTION

1. Field of the Invention

The present invention relates to an apparatus for white light observation and fluorescence diagnosis of skin diseases and, more particularly, to an apparatus for photodynamic diagnosis in which a plurality of excitation light emitting diodes (LEDs) is provided in an image pick-up head, the excitation LEDs being arranged to illuminate the entire examination region in the form of a mosaic by setting respective illumination light axes of the excitation LEDs to illuminate preassigned individual areas of the examination region, thus uniformly illuminating the examination region in a wide field of view with excitation light.

Moreover, the present invention relates to an apparatus for photodynamic diagnosis in which warm white LEDs and cold white LEDs as white light sources are appropriately arranged so as to deliver natural colors and thereby to reproduce natural color images.

2. Background Art

Recently, a variety of skin diagnosis apparatuses can be found in cosmetic shops, skin care clinics, and the like. With the skin diagnosis apparatus, a user can analyze and diagnose its skin condition so as to select cosmetics suitable for the skin condition or to find a problem in its skin condition and obtain a solution to the problem.

Among them, a skin diagnosis apparatus using a diagnostic lamp has been widely used for diagnosing the skin condition by irradiating a light beam of a predetermined wavelength onto the skin and analyzing a specific fluorescence emitted from the skin.

Conventional skin diagnosis apparatuses will be described with reference to literatures as follows.

Skin pores of a human body have sebaceous glands producing sebum, and the sebaceous glands in a healthy body secrete an appropriate amount of sebum from the skin pores to the skin surface to form a sebaceous membrane acting as a natural protecting layer.

However, an unhealthy body secretes an excessive amount of sebum and the sebum excessively secreted soon becomes oxidized by air, and the oxidized sebum becomes stickier and clogs the pores.

Bacteria propagate in the thus clogged pores and porphyrins are produced from the bacteria. The produced porphyrin emits light in response to ultraviolet light.

Accordingly, a skin diagnosis apparatus using porphyrin properties responsive to ultraviolet light has been developed.

The conventional skin diagnosis apparatus uses a method in which an ultraviolet lamp irradiates a patient's entire face in a dark box to observe a change in fluorescence intensities with naked eyes through a detector.

Moreover, optical fiber light sources based on the use of various kinds of lamp, such as halogen, xenon, metal-halide, mercury, etc., which are well known for the purpose of photodynamic diagnosis of diseases are developed and widely used.

Such lamps have been selected to meet the apparatus requirements in terms of specific medical purposes and means, technical and economical aspects. In a case where a complicated operation that should use a wide range of light intensities or a variety of light beams of selective wavelengths is required, the use of a single lamp could not provide an optimal method in general.

In this case, the developer of the apparatus has depended on a lamp having a specific function or used a plurality of lamps simultaneously to overcome the drawbacks. Especially, it has been known that it is necessary to observe geometry, position, color of an examination region by a white light in addition to the observation of fluorescence generated from the examination region by an excitation light irradiation in diagnosing diseases using fluorescence.

Advantages, possibilities and recent trends in use of fluorescence diagnosis (FD) and photodynamic therapy (PDT) of skin diseases using a photosensitizer including 5-aminolevulinic acid (5-ALA) have been described in the reference literature (C. Fritch and T. Ruzichka, "Fluorescence Diagnosis and Photodynamic Therapy of Skin Diseases", Atlas and Handbook, 2003, Springer-Verlag. Wien).

According to the literature, a fluorescence image of a dermal layer is recorded in the form of a photograph in such a manner that the examination region is exposed to ultraviolet light of a Wood's lamp in a dark room for 0.25 to 1.5 seconds to take a photograph and the photograph is developed with a high sensitivity film such as 1600 ASA.

Meanwhile, U.S. Pat. No. 5,363,854 has disclosed a method for detecting anomalies of the skin, more particularly melanoma, and an apparatus for carrying out the method, in which an ordinary video camera fixed with a light source in a picture processing unit is used for detecting a fluorescence picture of an examination region and a reference picture.

The apparatus includes a light source for illuminating a two-dimensionally extending examination region of the skin, successively, with ultraviolet light range and with visible light.

The camera records a fluorescence picture of the examination region having signal values $F(x,y)$ at its picture points $x,y$ in response to the illumination with ultraviolet light and a reference picture having signal values $R(x,y)$ at its picture points $x,y$ in response to the illumination with visible light.

Moreover, a memory stores the signal values of at least one of the fluorescence picture and said reference picture, and a processor responsive to the memory produces an output picture having respective signal values $A(x,y)$ at its picture points $x,y$ which are formed from respective quotients $F(x,y)/R(x,y)$ of the signal values of the fluorescence and reference pictures at the same picture points.

The image observed through an ocular of the apparatus is reorganized with two color images through a dichroic mirror, and the light source operates under continuous conditions or under impulse conditions and it saves energy and reduces the effect of extraneous light under the impulse conditions.

Moreover, the apparatus for detecting skin diseases includes an excitation light source for generating fluorescence from the examination region. The fluorescence generated along the reference light are divided by a beam splitter and sent to respective optical paths, the respective optical paths produce images in the examination region, and an optical coupler provides the images produced by the respective optical paths so that a user can observe the images with naked eyes.

U.S. Pat. No. 5,760,407 has proposed a device for the identification of acne, microcomedones, and bacteria on human skin.

Meanwhile, for the purpose of the diagnosis of skin diseases, there have been developed a series of photo-diagnostic methods using spectroscopy and imaging methods.

For the purpose of the skin therapy, there have been disclosed phototherapy methods by the action of electromagnetic radiation, and fluorescence diagnosis and photodynamic therapy (PDT) occupy an important place in such a series of photo-diagnostic methods.

In case of the fluorescence diagnosis, fluorescent characteristics observed in the diseased tissue region and in the normal tissue region are different from each other, and this difference is shown as emitted wavelength and fluorescence intensity.

One of the drawbacks in the spectroscopic wavelength calibration is that the spatial resolution in the examination region is low and the number of spots examined is small.

The method of obtaining the fluorescence image from the examination region eliminates the above drawback and the fluorescence images observed in most cases are given in the form of a monochrome fluorescence image.

Accordingly, for the purpose of an accurate morphological analysis, a color image acquired simultaneously by a white light from the same examination region is supplemented with the monochrome fluorescence image [simultaneous acquisition and display of morphological (color image) and physiological (fluorescence image) information] (DYADERM professional, Biocam GmbH; http://www.biocam.de].

However, as the monochrome fluorescence image loses information showing the difference of wavelengths in the individual skin regions, the quality of the image is substantially poor and it makes it difficult to investigate the cause of the fluorescence in study on the intrinsic fluorescence characteristics produced in the skin itself.

Meanwhile, it is possible to combine the advantages of the fluorescence spectroscopy method and the fluorescence imaging method by a multispectral imaging system [Hewett et al., 2000, "Fluorescence detection of superficial skin cancer," J. Mod. Opt. 47, 2021-2027].

Moreover, the basic spectroscopic information of the fluorescence produced from the skin can be obtained from the visible light range and thereby it is possible to apply a high sensitive color camera to the multispectral imaging system, thus simplifying the configuration of the apparatus and improving the spatial resolution as well.

Meanwhile, according to an apparatus for the white light observation and fluorescence diagnosis of skin diseases, it is possible to observe the skin tissue using an image pick-up head, and the image pick-up head includes an image pick-up device for picking-up an image of the skin through a view hole being in contact with the skin, and an illumination system.

In general, light emitting diodes (LEDs) having an illumination range of 395 nm to 405 nm have been used as fluorescence excitation light sources in the illumination system of the image pick-up head, and white LEDs have been used as white light sources.

Moreover, the field of view of the examination region, i.e., the region to be examined through the view hole, is generally about 20 mm. The light observation may be made through a television camera, for example, a color CCD-415: ½ inch, 782×582), and the image recording and image processing of the fluorescence and white light are simultaneously available.

As an excitation light source for exciting the fluorescence emitted from the diseased region, a diode that emits light in the ultraviolet range has been used. However, the light irradiation in the ultraviolet wavelength range has the following problems.

(1) As the excitation light is irradiated in the excitation wavelength range of collagen (320 nm to 380 nm), it is difficult to observe the fluorescence produced from other fluorescence sources of the skin due to a blue fluorescence in the vicinity of 400 nm produced from collagen extensively distributed in the skin.

(2) Since the main absorption band of porphyrins in Propionibacterium acnes is in the vicinity of a wavelength of 400 nm, the light efficiency for exciting the fluorescence is decreased.

(3) The ultraviolet rays used are harmful to the human body and hard to penetrate subcutaneous tissue.

Besides, if the ultraviolet LED lights are arranged circularly around the image pick-up light axis and the illumination light axes are collected to the center of the view hole, the illuminated regions by the LED lights should overlap each other based on the image pick-up light axis in order to obtain a UV illumination light of a uniform intensity in the view hole, and thereby the illuminated regions by the LED lights are limited to a very narrow range.

That is, if the LEDs are used as light sources, it has a basic problem of non-uniformity due to the characteristic that the illumination intensity is large in the center of the LEDs but becomes smaller as it comes nearer to the periphery.

Of course, in a case where a plurality of LEDs is arranged circularly in the image pick-up head, if the LEDs (excitation LEDs) 10 are arranged at the same illumination angle so that the illuminated regions overlap each other based on the light axis as shown in FIG. 6, the non-uniformity problem is somewhat solved. However, while the fluorescence image quality is satisfactory in the center of the field of view on the examination region, the image quality is still not good in the peripheral region due to insufficient illumination intensity. Especially, it is necessary to ensure a sufficient distance between the LEDs and the examination region, and thereby the illuminated regions by the LED lights are limited to a very narrow range.

If the sensitivity of the camera is increased to sufficiently illuminate the periphery, the central portion comes into a saturated condition.

Hereinafter, the non-uniformity problem of illumination in accordance with the conventional skin diagnosis apparatus will be described in more detail.

In order for the light emitting diode itself to provide a high uniformity of illumination, it is necessary to decrease the difference in intensities between the center of a spot illuminated by the LED and the boundary thereof, if possible.

Using RL-UV2030 (405 nm), one of the LEDs having excellent characteristics, as a sample LED, and varying the distance between the emission peak of the LED and the object region, the output densities in the spot center of the illumination beam according to the distances, and the diameters of the spots showing an intensity of 50% of the maximum intensity of the spot center were measured (using a detector with a diameter of 8 mm in an optical power meter Q8230), and the measurement results are shown in the following table 1:

TABLE 1

| | Distance between emission peak of LED and object region (mm) | | | | | | |
|---|---|---|---|---|---|---|---|
| | 20 | 25 | 30 | 35 | 40 | 45 | 50 | 55 |
| Output density (with filter) (mW/cm²) | 5.7 (4.27) | 4.6 (3.45) | 3.4 (2.55) | 2.6 (1.95) | 2.0 (1.5) | 1.5 (1.12) | 1.3 (0.97) | 1.1 (0.82) |
| Diameter at 50% intensity | 8.8 | 10.5 | 12.3 | 14.1 | 15.9 | 17.6 | 19.4 | 21.4 |

As can be seen from table 1, if a single LED is used to obtain an illumination required to observe the field of view, it is difficult to obtain a desired illumination.

That is, if the object region is illuminated from a close distance, the diameter of the illumination beam is insufficient, whereas, if illuminated from a far distance, the output density of the illumination beam is insufficient.

Accordingly, it is necessary to increase the number of LEDs so as to increase the output density of the illumination, and it may consider a variety of arrangements of the LEDs for a uniform illumination.

The simplest method is to employ, for example, twelve LEDs 10 in front of a camera 1 and to orient illumination light axes C2 of the LEDs 10 toward the center of the field of view as shown in FIG. 6. In this case, it is possible to obtain a uniform illumination as the diameter of the field of view is 21.4, in which the output density calculated in the center of the field of view is 9.9 mW/cm².

However, such an arrangement requires a considerable amount of free space from a fixing plate of the LEDs to the examination region, i.e., the view hole region, in the case of the image pick-up head, and from the LEDs to the examination region. Accordingly, it is necessary to ensure a sufficient distance from the LEDs to the examination region.

For example, such a distance should be more than 60 mm.

As a result, since the distance from the LEDs 10 to the view hole to be in contact with the examination region becomes long, it is inevitable that the entire length of the image pick-up head becomes long in order to ensure a sufficient distance.

Another method is to arrange the LEDs more adjacent to the view hole of the case in order to reduce the amount of free space by increasing the number of LEDs. The arrangement and illumination state of the LEDs used as excitation light sources in this case are shown in FIGS. 7 and 8.

In this case, twenty LEDs 10 are used as fluorescence excitation light sources, in which twelve LEDs are arranged around a circle with a diameter of 20 mm at regular intervals as shown in FIG. 7. Moreover, as shown in FIG. 8, the LEDs are arranged to have an angle α of 16° of an illumination light axis C2 based on an image pick-up light axis C1, i.e., a central axis of a camera 1, and arranged to have a distance of about 30 mm from the examination region, i.e., the view hole region.

The other eight LEDs are arranged around a circle with a diameter of 28 mm as shown in FIG. 7, in which each four LEDs is arranged in the left and light sides of the figure and inclined at the same angle as the twelve LEDs to have the same angle a of the illumination light axis C2. Moreover, the eight LEDs are positioned adjacent to the examination region, for example, about 8 mm closer than the twelve LEDs.

The additional eight LEDs arranged more adjacent to the examination region as described above are auxiliary illuminations for illuminating the left and right edge regions based on the pick-up light axis.

In such an arrangement, the rated current required for the respective LEDs is 20 mA, and 30 mA in maximum. The illumination output density in the center of the field of view that, i.e., in the center of the examination region, is 8.5 mW/cm² under the rated conditions (20 mA), and 12 mW/cm² under the forced condition (30 mA).

The images obtained from an examination region by such an illumination system are shown in A of FIG. 9. As shown in the figure, while the quality of the fluorescence image in the center of the field of view is relatively good, the quality of the peripheral image is not good due to insufficient illumination intensity.

FIG. 9 shows fluorescence images obtained from the illumination system in which the LEDs arranged circularly to illuminate at the same angle, in which 'A' is a fluorescence image taken from the examination region (gain 8, N=0, gamma=20, R=G=B=0) at 160 mA, and 'B' is a fluorescence image obtained by increasing the light sensitivity of a detector (camera) under the same conditions as 'A'.

Moreover, 'C' in FIG. 9 shows a fluorescence image of a standard model, in which contours are drawn at intensity intervals such as 30, 40, 50 and _70% of the maximum intensity. The diameters of the contours correspond to 72, 63, 54 and 40% of the diagonal size of the field of view (20.8 mm).

Furthermore, 'D' in FIG. 9 is a three-dimensional graphic showing an intensity distribution under the conditions of 'C'. If the camera sensitivity is increased to examine the periphery in more detail, the central portion comes into a saturated condition like the image of 'B', and such a non-uniformity of illumination is called the hot-spot. The hot-spot can be readily observed by the three-dimensional graphic for the illumination intensity (see 'D' of FIG. 9).

Meanwhile, if the illumination light of the LED is to have a Lambertian distribution, it is possible to provide a uniform illumination. However, since the Lambertian illumination distributes the light on a wide range, the output density of the light obtained from a specific examination region is relatively low and it is impossible to obtain a desired image.

In order to increase the output density of the illumination light for a desired image, a large number of LEDs are required, which results in an increase in size of the diagnosis apparatus.

Moreover, the output of the illumination light scattered by the LEDs in the Lambertian illumination heats the case and the other components of the apparatus, which may cause a burn injury or discomfort to a patient.

SUMMARY OF THE INVENTION

The present invention has been made in an effort to solve the above problems, and an object of the present invention is to provide an apparatus for photodynamic diagnosis, in which a plurality of excitation light emitting diodes (LEDs) is provided in an image pick-up head, the excitation LEDs being arranged to illuminate the entire examination region in the form of a mosaic by setting respective illumination light axes of the excitation LEDs to illuminate preassigned individual areas of the examination region, thus uniformly illuminating the examination region in a wide field of view with excitation light.

Moreover, another object of the present is to provide an apparatus for photodynamic diagnosis in which warm white LEDs and cold white LEDs as white light sources are appropriately arranged so as to deliver natural colors and thereby to reproduce natural color images.

In an aspect, the present invention provides an apparatus for photodynamic diagnosis, in which a plurality of white light emitting diodes (LEDs) used as white light sources and a plurality of excitation LEDs used as fluorescence exciting light sources are provided in a case of an image pick-up head for white light observation and fluorescence diagnosis on an examination region, the apparatus for photodynamic diagnosis being characterized in that the respective excitation LEDs are arranged to have a predetermined illumination light axis angle based on an image pick-up light axis such that the plural excitation LEDs illuminate preassigned individual areas of the examination region being in contact with a view hole in front of the case of the image pick-up head in the form of a mosaic combining the preassigned individual areas.

Preferably, each of the fluorescence excitation LEDs is an LED that uses a visible light wavelength of 400 nm.

Suitably, the plural LEDs using a visible light wavelength of 400 nm as fluorescence excitation LEDs are arranged circularly or rectangularly based on the image pick-up light axis.

Moreover, the plural LEDs used as white light sources are arranged such that warm white light source LEDs having a strong red component and cold white light source LEDs having a strong blue component are alternated.

Furthermore, the warm white light source LEDs and the cold white light source LEDs are arranged circularly or rectangularly outside the fluorescence excitation LEDs.

In addition, the warm white light source LEDs and the cold white light source LEDs are alternately arranged one by one.

In another aspect, the present invention provides an apparatus for photodynamic diagnosis, in which a plurality of white light emitting diodes (LEDs) used as white light sources and a plurality of excitation LEDs used as fluorescence exciting light sources are provided in a case of an image pick-up head for white light observation and fluorescence diagnosis on an examination region, the apparatus for photodynamic diagnosis being characterized in that the plural LEDs used as white light sources are arranged such that warm white light source LEDs having a strong red component and cold white light source LEDs having a strong blue component in light spectrum are alternated.

Preferably, the warm white light source LEDs and the cold white light source LEDs are arranged circularly outside the fluorescence excitation LEDs.

Suitably, the warm white light source LEDs and the cold white light source LEDs are alternately arranged one by one.

DETAILED DESCRIPTION OF THE INVENTION

Figure 1:
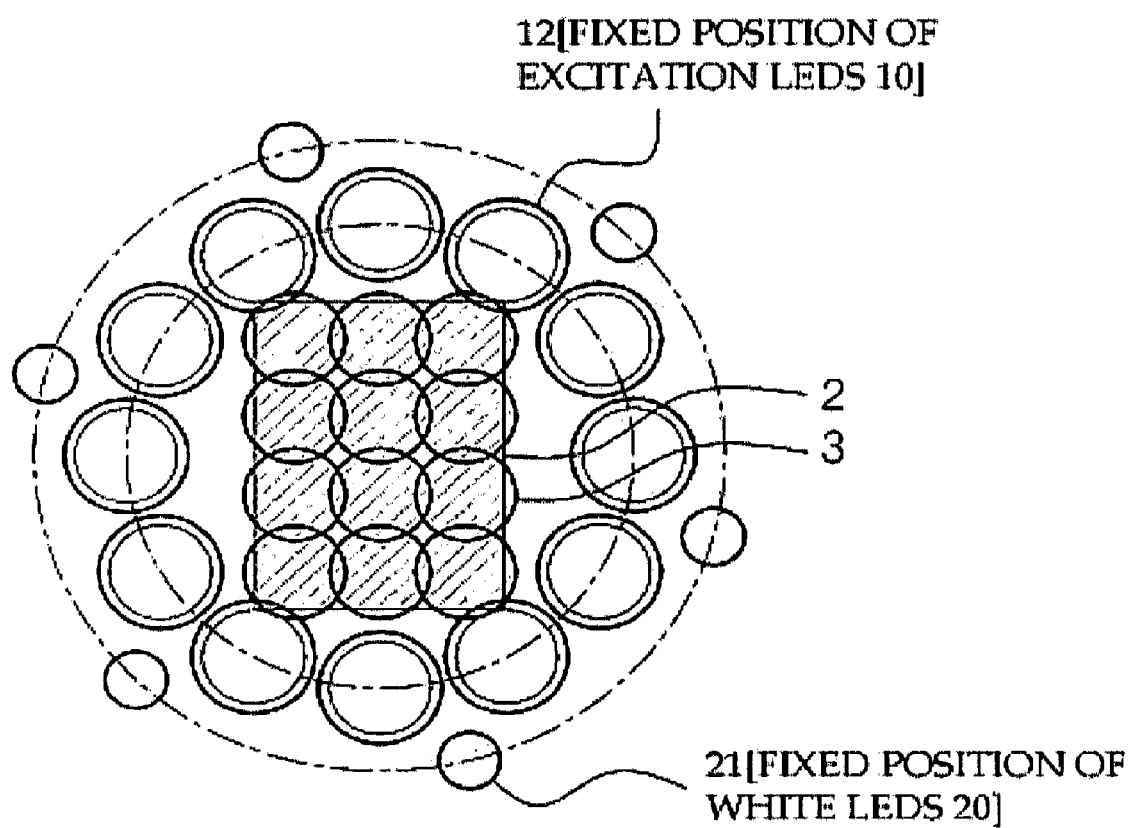
FIG. 1 shows an arrangement and illumination state of excitation light sources and white light sources in an apparatus for photodynamic diagnosis in accordance with the present invention.

Reference will now be made in detail to the preferred embodiment of the present invention, examples of which are illustrated in the drawings attached hereinafter, wherein like reference numerals refer to like elements throughout. The embodiments are described below so as to explain the present invention by referring to the figures.

The present invention provides an apparatus for white light observation and fluorescence diagnosis of skin diseases. More particularly, the present invention provides an apparatus for photodynamic diagnosis that improves the uniformity of illumination using light emitting diodes (LEDs).

Especially, the apparatus for photodynamic diagnosis of the present invention optimizes the light emitting directions of the LEDs arranged in an image pick-up head to improve uniformity of illumination. That is, the arrangement of LEDs is optimized so that the illumination in the form of a mosaic is provided in the illumination of the field of view, i.e., in the skin region to be observed and examined through a view hole.

First, a light emitting diode LED that uses the visible light in the vicinity of a wavelength of 400 nm, which is the maximum absorption band of fluorescence dyes such as porphyrins in Propionibacterium acnes, 5-aminolevulinic acid (5-ALA), and the like, is used as an excitation light source for exciting fluorescence.

With the use of such an LED, it is possible to improve the light absorption efficiency and, especially, since the wavelength of the illumination light used does not correspond to the excitation light range of collagen, it is possible to exclude blue fluorescence scattered extensively, thus readily observing fluorescence produced from subcutaneous tissue, capillary, and the like.

As an object of the present invention is to improve the uniformity of fluorescence images with an appropriate arrangement of the LEDs, it is necessary to consider the areas occupied by the LEDs and optical filters as well as the limitations related to the size of various parts additionally provided. Considering given limitations, a desired configuration for obtaining a uniform fluorescence image is shown in FIGS. 1 to 3.

Figure 2:
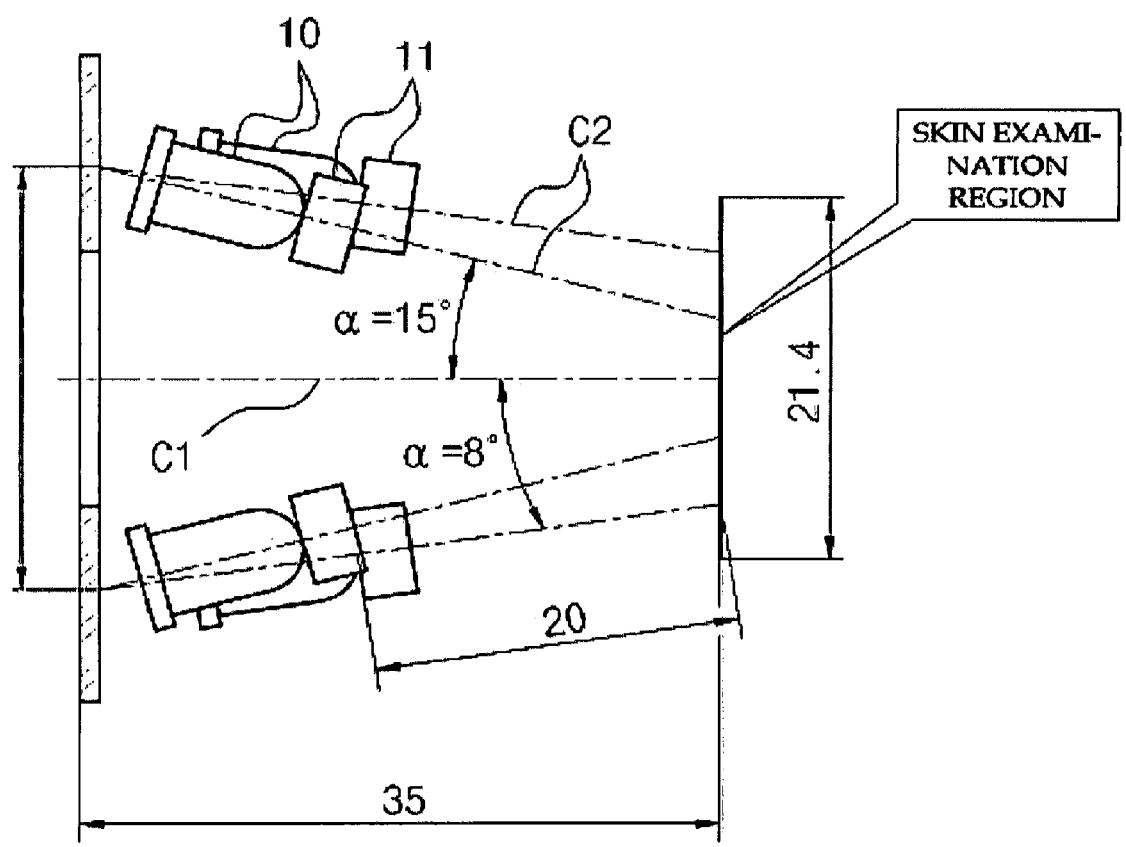
FIG. 2 is a diagram illustrating excitation light sources in an apparatus for photodynamic diagnosis in accordance with the present invention.
Figure 3:
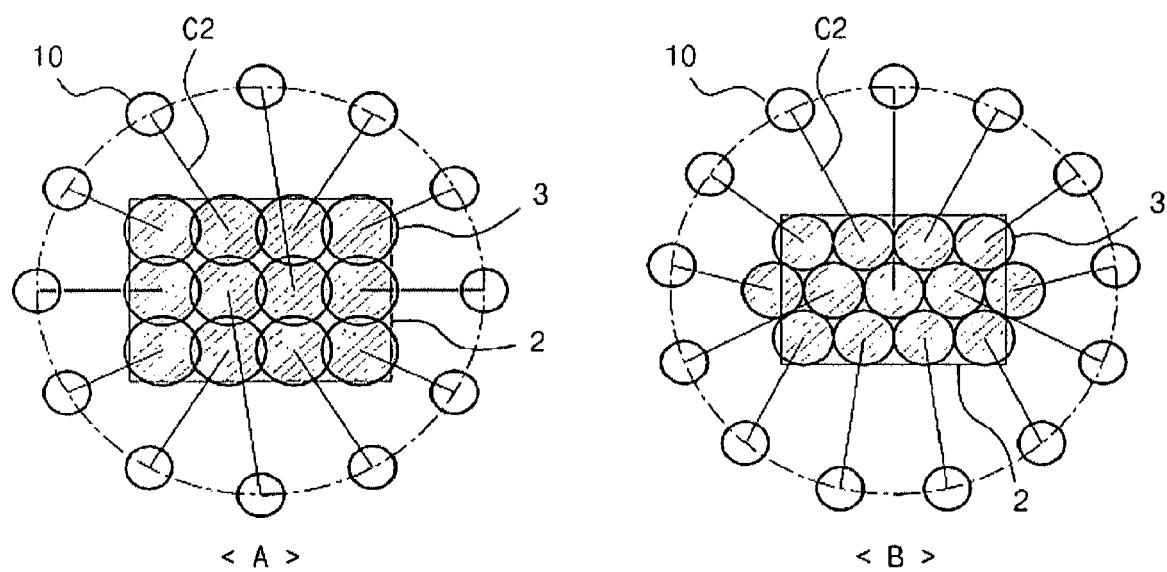
FIG. 3 shows two examples of a mosaic illumination in accordance with the present invention, in which twelve LEDs are used in 'A' and thirteen LEDs are used in 'B'.
Figure 4B:
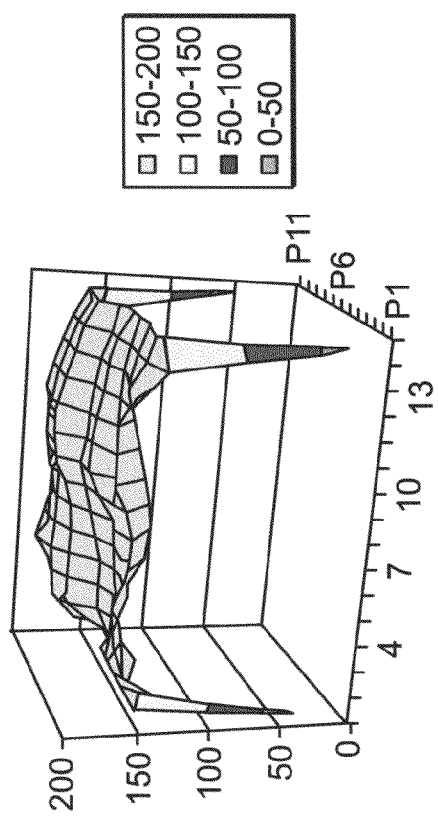
FIG. 4 shows fluorescence images obtained from a standard model and an examination region, from which fluorescence is uniformly emitted, using an apparatus for photodynamic diagnosis to which a mosaic illumination in accordance with the present invention is applied.
Figure 4D:
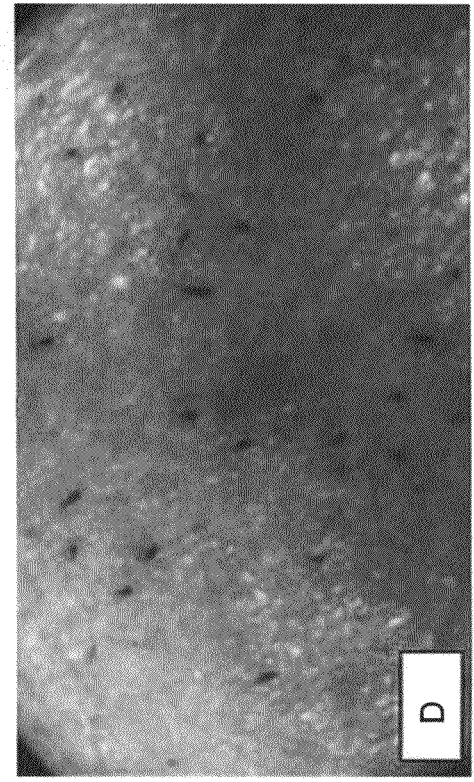
Figure 4A:
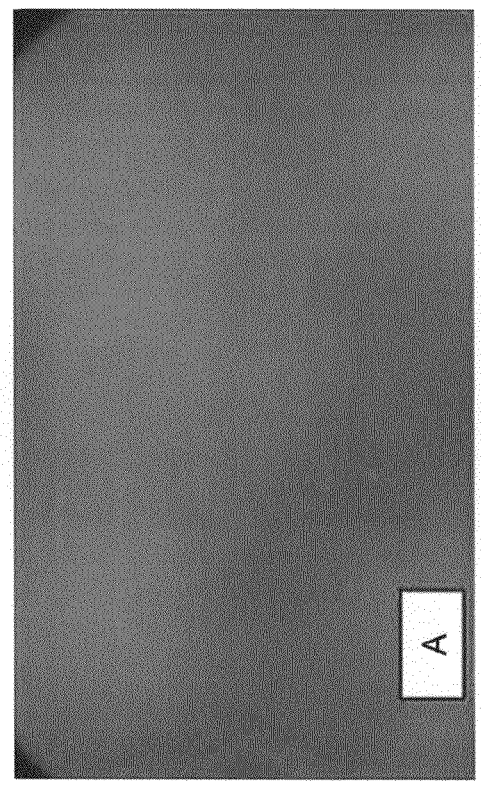
Figure 4C:
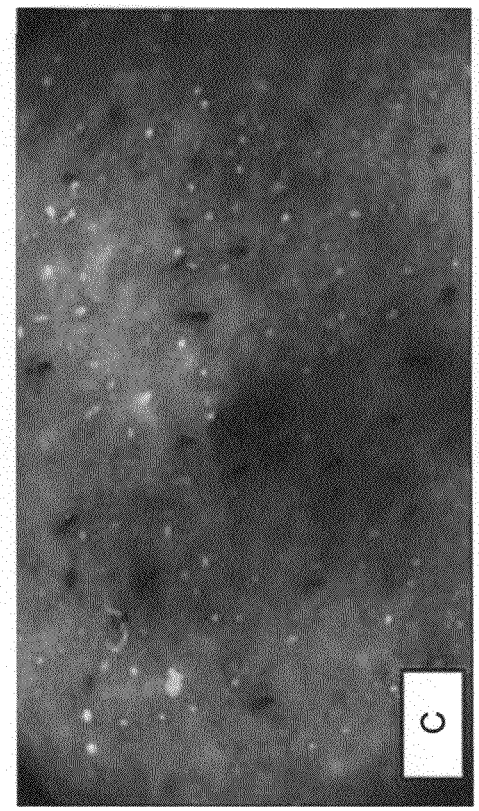
Figure 5A:
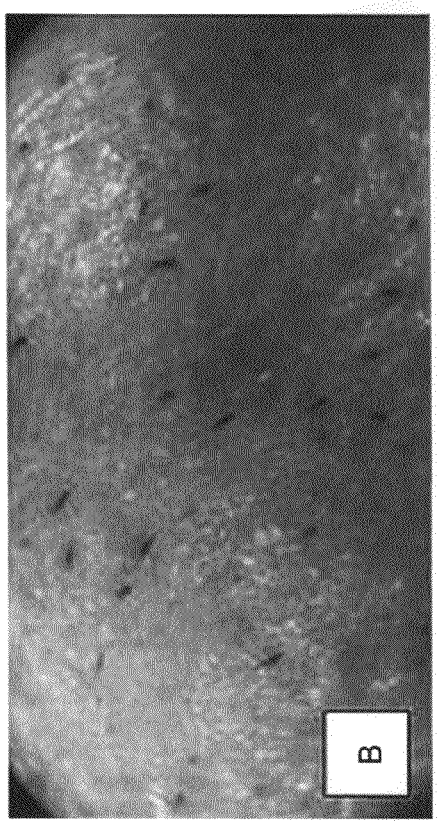
FIG. 5 shows color images obtained from the same skin region by different white LEDs.
Figure 5B:
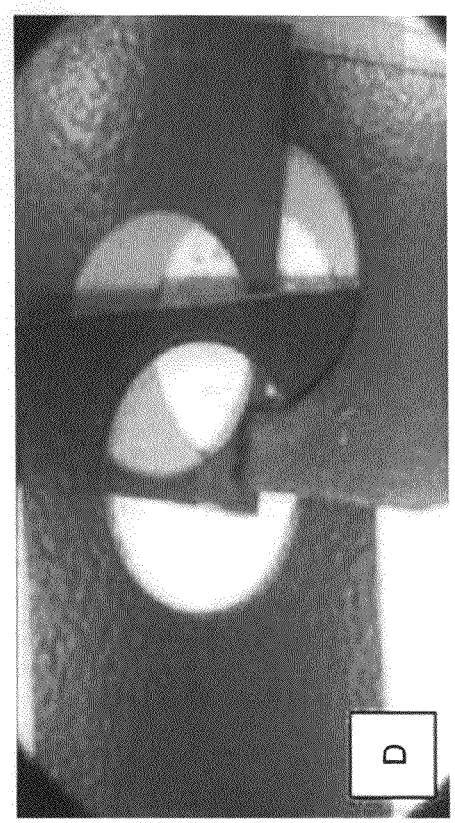
Figure 5C:
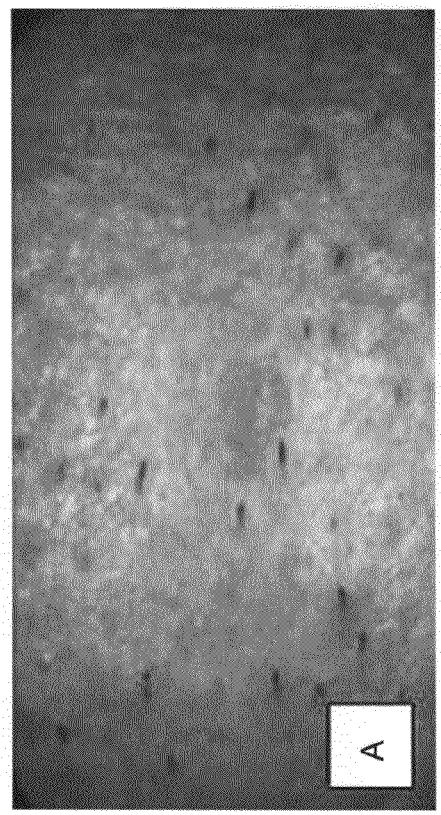
Figure 5D:
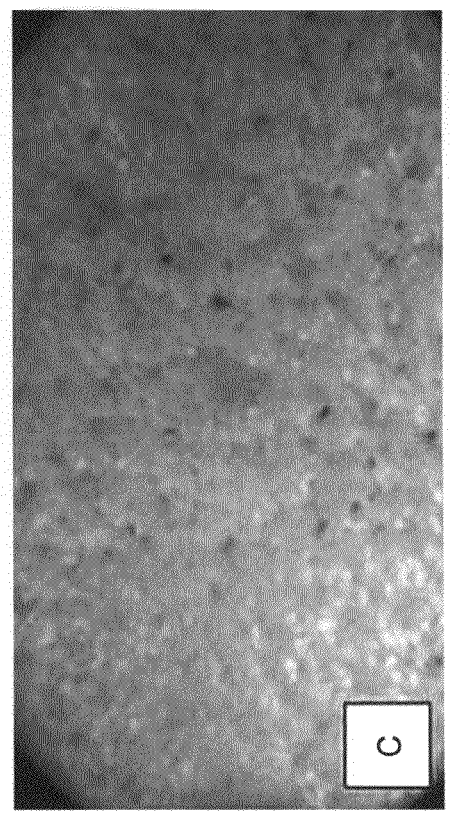
Figure 6:
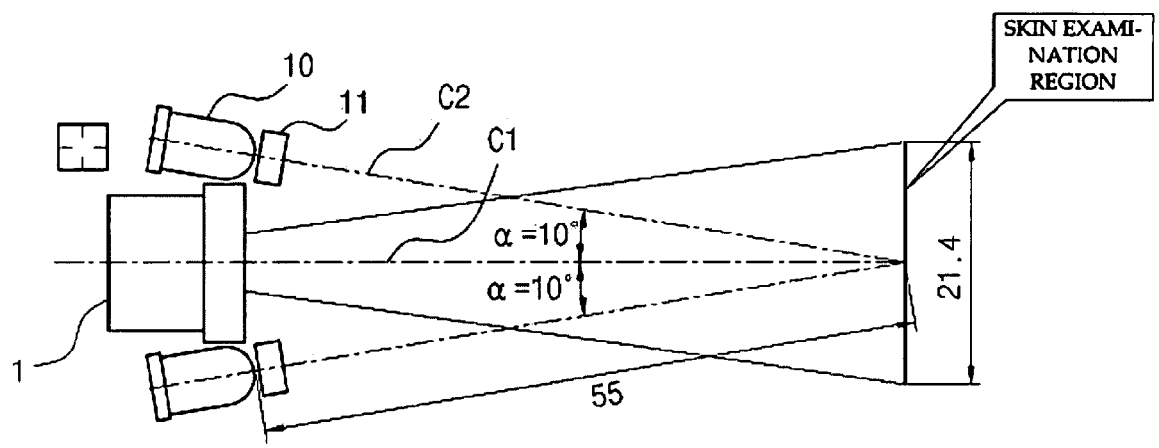
FIG. 6 a diagram illustrating excitation light sources in a conventional apparatus for photodynamic diagnosis.
Figure 7:
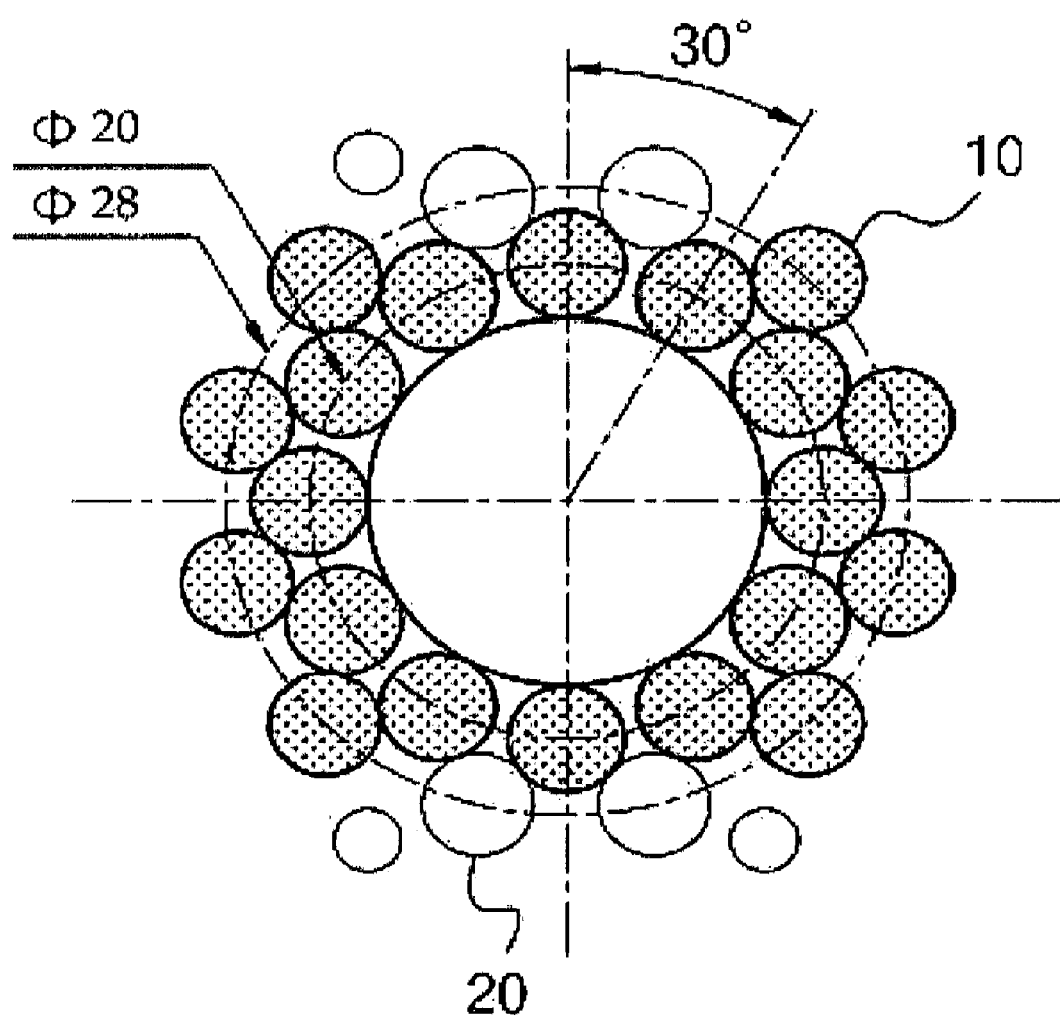
FIGS. 7 and 8 an arrangement and illumination state of LEDs used as excitation light sources in a conventional apparatus for photodynamic diagnosis.
Figure 8:
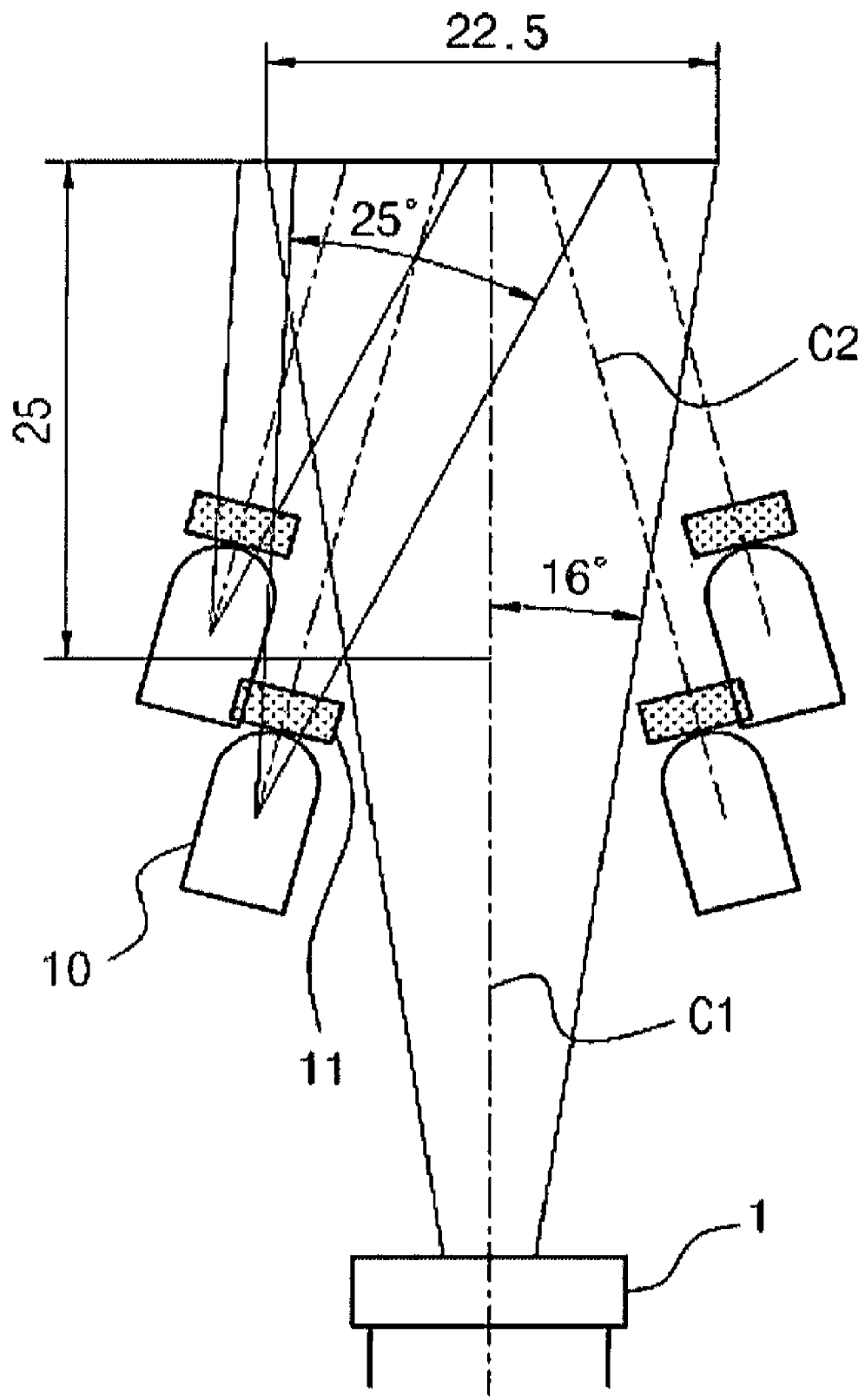
Figure 9B:
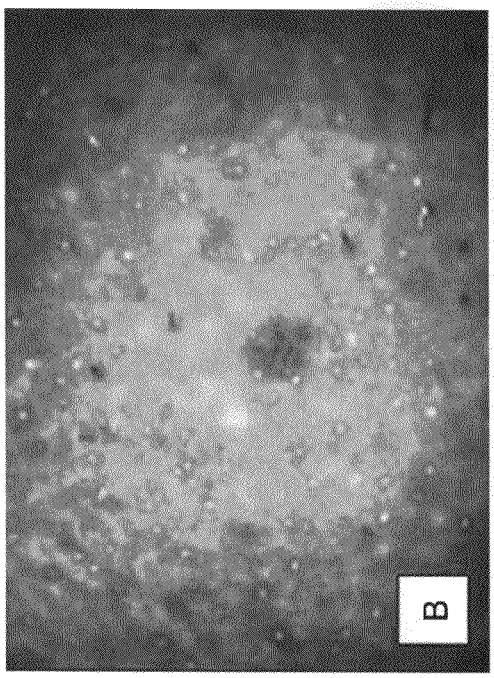
FIG. 9 shows fluorescence images obtained from an illumination system in which LEDs arranged circularly illuminate at the same angle.
Figure 9D:
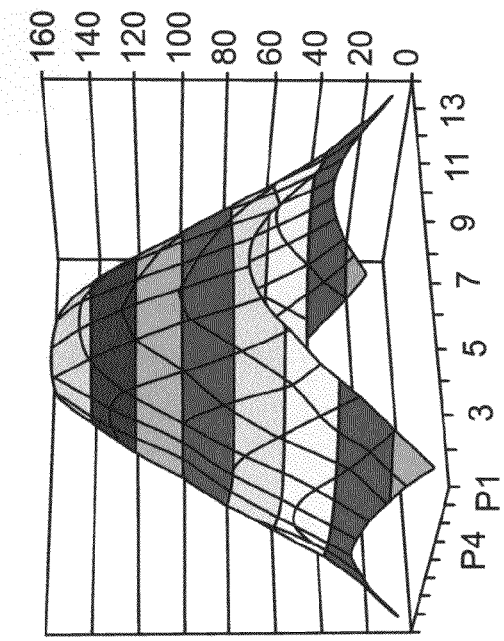
Figure 9A:
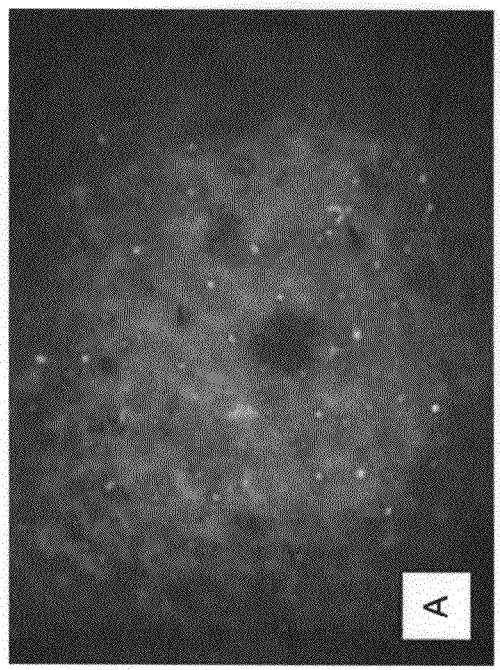
Figure 9C:
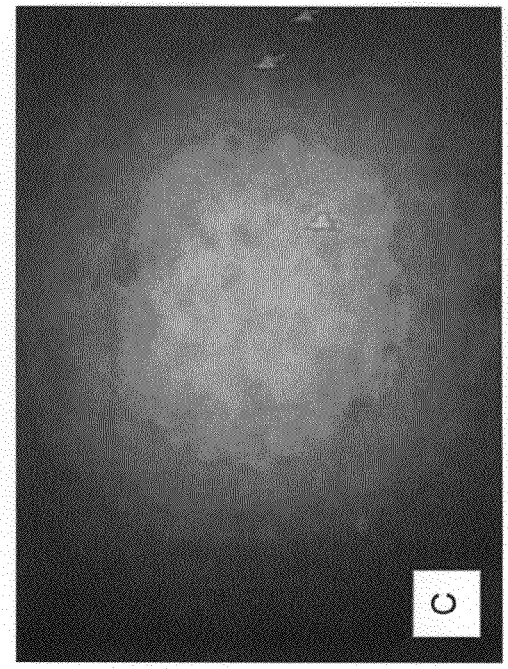

FIG. 1 shows an arrangement and illumination state of excitation light sources and white light sources arranged circularly based on an image pick-up light axis, i.e., a camera axis, in a case of an image pick-up head in an apparatus for photodynamic diagnosis in accordance with the present invention, FIG. 2 is a diagram illustrating excitation light sources arranged circularly in the case of the image pick-up head in an apparatus for photodynamic diagnosis in accordance with the present invention, and FIG. 3 shows two examples of a mosaic illumination in accordance with the present invention, in which twelve LEDs are used in 'A' and thirteen LEDs are used in 'B'.

In the apparatus for photodynamic diagnosis, a plurality of excitation LEDs used as excitation light sources is arranged in front of a camera 1 to illuminate the examination region through a view hole formed in the front end of the case. As shown in the figures, the respective excitation LEDs 10 are arranged to provide an illumination in the form of a mosaic on the examination region.

In order to apply such a mosaic illumination to a preferred embodiment of the present invention, the plural excitation LEDs 10 are arranged in a predetermined shape such as a circle, a rectangle, etc. based on an image pick-up light axis C1, i.e., a central axis of a camera 1, at regular intervals in the case of the image pick-up head as shown in FIGS. 1 to 3. Moreover, the respective excitation LEDs 10 are provided at the same or different angle α of the illumination light axis C2 based on the image pick-up light axis C1.

Especially, in the apparatus for photodynamic diagnosis, the angles α of the illumination light axes C2 are adjusted such that the respective excitation LEDs 10 illuminate the preassigned individual areas of the examination region being in contact with the view hole in the front end of the case as shown in FIGS. 1 to 3. Accordingly, the plural excitation LEDs 10 provided in the case can illuminate the entire examination region in the form of a mosaic combining the preassigned individual areas.

Referring to FIG. 1 showing the arrangement state of the excitation LEDs 10 for the mosaic illumination, a concentric circle 12 in doublet with a diameter of 5 mm and 6 mm denotes the fixed position of the excitation LEDs 10 for exciting fluorescence. A rectangle 2 denotes a field of view region, i.e., a view hole region of the image pick-up head, which corresponds to the examination region being in contact with the view hole, and denotes a region where a uniform illumination should be provided by the excitation LEDs 10 for the diagnosis. In FIGS. 1 and FIG. 2, a plurality of LEDs (10) (both white and excitation) are arranged around the camera at various angles. As can be seen in FIG. 1, the angle alpha is directly related to the angle of the LED thus, the LEDs are arranged at various angles as well around the camera.

Circles 3 marked by thin oblique lines denote the region illuminated by the respective LEDs 10, i.e., the region where the respective LEDs 10 illuminate the preassigned individual areas in the entire examination region. The areas that the respective LEDs 10 illuminate are determined by the angles α of the illumination light axes C2 based on the image pick-up light axis C1.

The centers of the circles 3 marked by the oblique lines correspond to intersections between the illumination light axes C2 and the surfaces of the examination regions.

Light emitting diodes (LEDs) 20 used as white light sources for obtaining a color image are arranged in a predetermined shape such as a circle, a rectangle, etc. outside the arrangement of the excitation LEDs 10. In FIG. 1, a circle 21 with a diameter of 3 mm arranged outside denotes the fixed position of the white light sources. In FIG. 2, there are shown that the respective excitation LEDs 10 are arranged based on the image pick-up light axis C1 by varying the angles α of the illumination light axes C2. For the mosaic illumination, the respective LEDs 10 should illuminate the preassigned individual areas in the region of the field of view. Accordingly, the angles α of the illumination light axes C2 of the respective LEDs 10 are set separately.

Reference numeral 11 in FIG. 2 denotes excitation filters.

FIG. 3 shows two examples in which a plurality of LEDs 10 are arranged circularly in the apparatus for photodynamic diagnosis and the mosaic illuminations are provided on the field of view of the examination region in order to improve the uniformity of illumination.

The number of the excitation LEDs 10 may be appropriated adjusted. That is, in a case where a total of twelve LEDs 10 are used like 'A' in FIG. 3, the light emitting directions of the respective LEDs may be set to provide a mosaic illumination on a rectangular region as a whole (rectangular mosaic illumination). In a case where a total thirteen LEDs 10 are used like 'B' in FIG. 3, the light emitting directions of the respective LEDs may be set to provide a mosaic illumination on a hexagonal region as a whole (hexagonal mosaic illumination).

Like this, according to the apparatus for photodynamic diagnosis of the present invention, the plural excitation LEDs 10 are provided at various angles based on a light axis of an object lens, i.e., the image pick-up light axis that becomes a camera axis, to illuminate the field of view of the examination region individually. Accordingly, it is possible that the beams of the light sources composed of the LEDs illuminate the field of view of the examination region uniformly, thus improving the uniformity of illumination.

FIG. 4 shows fluorescence images obtained from a standard model and an examination region, from which fluorescence is uniformly emitted, using an apparatus for photodynamic diagnosis to which the mosaic illumination in accordance with the present invention is applied, in which 'A' is a fluorescence image taken from the standard model, 'B' is a three-dimensional graphic showing a fluorescence intensity distribution of the standard model, 'C' is a fluorescence image of the examination region (gain 8, N=0, gamma=20, R=G=B=0) at 160 mA, and 'D' is a white light image of the same examination region.

A red line in 'A' showing the fluorescence image of the standard model in FIG. 4 is a boundary line showing an intensity level of 70% of the maximum fluorescence value, and the fluorescence intensity of the standard model can be seen from the three-dimensional graphic of 'B'.

Referring to 'A' and 'B' of FIG. 4, most field of view is positioned within the boundary line, and it can be seen that, if the illumination system with the mosaic illumination is applied, it is possible to considerably improve the uniformity of illumination compared with the conventional illumination system.

Moreover, according to the illumination system of the present invention, it is possible to provide a desired fluorescence image 'C' due to the close distance between the LEDs and the examination region, even if a smaller number of LEDs are used.

LEDs 10 having a wavelength in the vicinity of 400 nm were used to as excitation light sources obtain the fluorescence image of FIG. 4, and shortpass or bandpass excitation filters 11 were provided in front of the LEDs 10 to improve the contrast of the fluorescence image (see FIG. 2). Here, the excitation filters 11 are used to remove parasitic fluorescence generated from the lens provided on the top portion of the excitation LEDs 10.

Moreover, it is possible to surround the lateral side of the excitation LED with an opaque tube resistant to heat.

Meanwhile, it is possible to provide a barrier filter in front of a light detector, i.e., a CCD television camera, to prevent the entrance of the excitation light reflected from the skin into the light detector.

The barrier filter removes on the light path toward the detector while the LEDs used as white light sources are turned on, thus improving the color quality of the image obtained with the white light.

A sufficient intensity and uniformity in the white light illumination can be readily obtained. That is, it is sufficient that the white LEDs be provided in the four corners of the field of view in the examination region and the white LEDs produce a diffuse illumination.

Under white light conditions, the difficult thing is to deliver accurate colors, and the white light does not exhibit a uniform intensity over the entire visible light range in general.

Such a difference in intensities due to the wavelengths is determined by luminescent compositions. In case of the white LEDs, there may exist a wavelength range showing a stronger intensity in the visible light range.

For example, in light spectrum, a red component (warm white) is stronger in case of HB3b-449 AWD (Huey Jann El., Taiwan—hueyjann.com), whereas, a blue component (cold white) is superior in case of BL-BZ43V1 (Bright Led Electronics corp., Taiwan).

In the apparatus for photodynamic diagnosis of the present invention, wherein a plurality of LEDs 20 is arranged circularly or rectangularly, warm white light source LEDs having a strong red component and cold white light source LEDs having a strong blue component are appropriately arranged.

That is, the warm white light source LEDs and the cold white light source LEDs are alternately arranged to deliver more natural colors under white light conditions. Accordingly, with the alternate arrangement of the white LEDs, it is possible to obtain a more excellent color image.

Here, the warm white light source LEDs and the cold white light source LEDs may be alternately arranged one by one.

Moreover, the white light sources may produce a diffuse illumination for a uniform illumination.

FIG. 5 shows color images obtained from the same skin region by different white LEDs, in which 'A' is a color image taken using the warm white LEDs (HB3b-449 AWD) having a strong red component, 'B' is a color image taken using the cold LEDs (BL-BZ43V1) having a strong blue component, and 'C' is a color image obtained (gain 8, N=0, gamma=20, R=G=B=0) in the alternate arrangement of the warm while LEDs and the cold white LEDs (HB3b-449 AWD+BL-BZ43V1) in accordance with the present invention.

It can be seen from image 'A' reproduced generally in red tone and image 'B' displayed in blue tone that the natural colors are not expressed.

However, with the alternate arrangement of the warm white LEDs and the cold white LEDs, it is possible to obtain a color image reproduced in natural colors as can be seen from image 'C'.

In the apparatus for photodynamic diagnosis configured as described above, the fluorescence image and the white light image obtained through the camera overlap each other by pixels with the help of the computer in order to explicitly examine the tissue state, and can be seen by transparency through a computer display.

Moreover, the display device displaying the images may be provided directly in the image pick-up head, i.e., in the camera head of the apparatus for photodynamic diagnosis for convenience' sake of diagnosis. Furthermore, the optical system of the camera head may include a precise focusing device in order to obtain a precise image of the skin region positioned outside the view hole surface of the camera head.

In addition, the precise focusing device can be achieved with an electronic driving device or an automatic focusing device for convenience's sake of operation, and the camera head may include an optical system or a digital zoom system in order to distinguish the skin region with various magnifications.

As described above, the apparatus for photodynamic diagnosis in accordance with the present invention has the following advantages compared with the conventional apparatus:

(1) Since a plurality of excitation light emitting diodes (LEDs) is provided in an image pick-up head, the excitation LEDs being arranged to illuminate the entire examination region in the form of a mosaic by setting respective illumination light axes of the excitation LEDs to illuminate preassigned individual areas of the examination region, it is possible to uniformly illuminate the examination region in a wide field of view with excitation light. Moreover, the respective excitation LEDs are provided at the same or different angles based on the light axis of the object lens, and thereby it is possible that the beams of the light sources composed of the LEDs illuminate the field of view of the examination region uniformly, thus improving the uniformity of illumination.

(2) Since the excitation LEDs that uses the visible light in the vicinity of a wavelength of 400 nm, which is the maximum absorption band of fluorescence dyes such as porphyrins in Propionibacterium acnes, 5-aminolevulinic acid (5-ALA), and the like, are used as excitation light sources, it is possible to observe the fluorescence emitted from subcutaneous tissue, capillary, and the like with high quality fluorescence images.

(3) With the uniform illumination lights, it is possible to provide a quantitative observation of light intensity as well as a simple observation of the examination region.

(4) With the alternate arrangement of the warm white LEDs and the cold white LEDs as white light sources, it is possible to deliver natural colors. That is, it is possible to obtain a natural color image thanks to the appropriate color combination made in accordance with color characteristics of the white LEDs.

(5) Since the fluorescence overlaps the white light background, it is possible to accurately determine the position where the fluorescence is produced.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. An apparatus for photodynamic diagnosis, comprising a camera device:
   a plurality of white light emitting diodes (LEDs) used as white light sources and a plurality of excitation LEDs used as fluorescence exciting light sources, wherein the plurality of white LEDs and excitation LEDs are arranged around and in front of the camera device and concentrate light on an object from white and excitation LEDs oriented at various angles for white light observation and fluorescence diagnosis on an examination region,
   wherein the respective excitation LEDs are arranged to have a predetermined illumination light axis angle based on a light axis of the camera such that the plurality of excitation LEDs illuminate preassigned individual areas of the examination region being in contact with a view hole in front of the case of the camera in the form of a mosaic combining the preassigned individual areas.

2. The apparatus of claim 1, wherein each of the fluorescence excitation LEDs is an LED that emits at visible light wavelength of about 400 nm.

3. The apparatus of claim 1 wherein the plurality of LEDs emit at a visible light wavelength of about 400 nm as fluorescence excitation LEDs are arranged circularly or rectangularly based on the camera light axis.

4. The apparatus of claim 1, wherein the plurality of LEDs used as white light sources are arranged such that warm white light source LEDs having a strong red component and cold white light source LEDs having a strong blue component in light spectrum are alternated.

5. The apparatus of claim 4, wherein the warm white light source LEDs and the cold white light source LEDs are arranged circularly or rectangularly outside the fluorescence excitation LEDs.

6. The apparatus of claim 4 wherein the warm white light source LEDs and the cold white light source LEDs are alternately arranged one by one.

7. An apparatus for photodynamic diagnosis, comprising:
a camera device;
a plurality of white light emitting diodes (LEDs) arranged around and in front of the camera device, the plurality of white LEDs used as white light sources provided in a case of the cameras device and concentrate light on an object from white and excitation LEDs oriented at various angles on an object, for white light observation on an examination region; and
a plurality of excitation LEDs arranged around and in front of the camera device and concentrate light from the plurality of the excitation LEDs oriented at various angles on the object, the plurality of excitation LEDs used as fluorescence exciting light sources, the plurality of excitation LEDs provided in a case of the camera device for fluorescence diagnosis on the examination region,
wherein the respective excitation LEDs are arranged to have a predetermined illumination light axis angle based on the camera light axis such that the plurality of excitation LEDs illuminate preassigned individual areas of the examination region being in contact with a view hole in front of the case of the camera device in the form of a mosaic combining the preassigned individual areas.

8. The apparatus of claim 7, wherein each of the fluorescence excitation LEDs is an LED that emits at visible light wavelength of about 400 nm.

9. The apparatus of claim 7 wherein the plurality of LEDs emit at a visible light wavelength of about 400 nm as fluorescence excitation LEDs are arranged circularly or rectangularly based on the camera light axis.

10. The apparatus of claim 7 wherein the plurality of LEDs used as white light sources are arranged such that warm white light source LEDs having a strong red component and cold white light source LEDs having a strong blue component in light spectrum are alternated.

11. The apparatus of claim 7 wherein the warm white light source LEDs and the cold white light source LEDs are arranged circularly or rectangularly outside the fluorescence excitation LEDs.

12. The apparatus of claim 7 wherein the warm white light source LEDs and the cold white light source LEDs are alternately arranged one by one.

* * * * *